(12) United States Patent
de Coulon

(10) Patent No.: US 6,476,605 B1
(45) Date of Patent: Nov. 5, 2002

(54) INDUCTIVE SENSOR FOR TARGET PARAMETER DETECTION AND MAGNETIC IMAGE FEATURE DETERMINATION

(75) Inventor: Yves de Coulon, Thielle-Wavre (CH)

(73) Assignee: CSEM Centre Suisse d'Electronique et de Microtechnique SA (CH)

( * ) Notice: Subject to any disclaimer, the term of this patent is extended or adjusted under 35 U.S.C. 154(b) by 0 days.

(21) Appl. No.: 09/524,546

(22) Filed: Mar. 13, 2000

(30) Foreign Application Priority Data

Mar. 11, 1999 (CH) ............................................. 0451/99

(51) Int. Cl.$^7$ .............................. G01B 7/30; G01P 3/42; G01P 3/46; G01P 21/00; G01N 27/72
(52) U.S. Cl. ..................... 324/243; 324/163; 324/173; 324/202; 324/207.17; 324/242; 702/94; 702/96; 702/145; 702/196
(58) Field of Search ................................ 324/202, 233, 324/239–243, 207.17–207.19, 207.25, 163, 164, 173; 702/94–96, 142, 145–148, 150, 167, 191–196

(56) References Cited

U.S. PATENT DOCUMENTS

| 3,469,182 A | * | 9/1969 | Wycherley et al. ..... 324/242 X |
| 3,875,502 A | * | 4/1975 | Neumaier ................ 324/242 X |
| 4,990,851 A | * | 2/1991 | Spies ...................... 324/242 X |
| 5,262,722 A | * | 11/1993 | Hedengren et al. ......... 324/242 |
| 5,510,709 A | * | 4/1996 | Hurley et al. ................ 324/242 |
| 6,288,538 B1 | * | 9/2001 | Aruga et al. ............ 324/242 X |

FOREIGN PATENT DOCUMENTS

| CH | 673896 | * | 4/1990 | .................. 324/242 |
| JP | 56-154687 | * | 11/1981 | .................. 324/243 |

* cited by examiner

Primary Examiner—Gerard R. Strecker
(74) Attorney, Agent, or Firm—Parkhurst & Wendel, L.L.P.

(57) ABSTRACT

Inductive sensor for non-contact detection of discontinuities of a conductive or ferromagnetic target for determination of target position, movement and speed, or generally of a magnetic image, including a plurality of receiving secondary windings associated with each exciting primary winding, configured to obtain electric signals optimized as a function of the discontinuities of the target. The sensor, combined with a suitable electric measuring circuit, allows global analysis of the signals provided by the secondary windings and configuration of a network in accordance with a predefined selection. An adaptive circuit allows auto-calibration of the sensor.

8 Claims, 4 Drawing Sheets

INDUCTIVE SENSOR FOR TARGET PARAMETER DETECTION AND MAGNETIC IMAGE FEATURE DETERMINATION

FIELD OF THE INVENTION

The invention relates to inductive sensors of planar type, which allow detection of the discontinuities of a conductive or ferromagnetic part (or target) without contact therewith.

BACKGROUND OF THE INVENTION

Magnetic induction sensors of planar type are known and are described in European Patent Applications No. 97 106 884.6 and No. 98 400 835.9 for example. Such a miniaturized inductive sensor comprises at least one primary winding traversed by an alternating current which creates an alternating magnetic field and at least one secondary winding subject to this alternating field, the windings being planar. The amplitude and the phase of the magnetic flux passing through each secondary winding are modified by the passage of a metallic or ferromagnetic part (or target) having at least one discontinuity, such that the passage of this discontinuity is detected by measuring the amplitude or phase modulation of the electric voltages induced in the secondary windings, which allows determination of the type of discontinuity and the sense and speed of the movement of the metallic part through suitable processing of the signals representing these voltages.

Such sensors are used in many fields and, particularly in the field of automobiles, to detect the speed of rotation of the engine shaft or of wheels, by means of a toothed wheel for example, whose teeth pass in front of the inductive sensor, which creates variations in the voltage induced in the secondary windings during the passage of the flanks of the teeth. The amplitude of the variations depends strongly on the position and orientation of the sensor relative to the target. Thus the geometry of the coils and the mounting of the sensor are adapted to the shape of the teeth, or marks, of the target.

In most applications, the inductive sensor has to be located with precision relative to the target, so as to obtain a satisfactory electric signal, for example with as high as possible a signal-to-noise ratio, to ensure good detection even in the presence of noise introduced by the elements used to process the signal. Such precise positioning of the sensor relative to the target is difficult to effect however, or holding its position with the passage of time cannot always be ensured and the initial adjustment then gets modified.

One object of the present invention is thus to provide an inductive sensor which allows the signal-to-noise ratio to be optimized, even in the event of non-optimal positioning of the sensor relative to the target.

Another object of the present invention is also to provide an inductive sensor whose positioning relative to the target is simpler, cheaper, more rapid, more reliable and thus less troublesome.

A further object of the invention is to allow the use of a large number of receiving coils whose output signals are processed in an overall manner in such a way as to allow information to be recovered, for example on the shape of the discontinuity of the target (magnetic image), or the position or the movement of a predetermined shape.

SUMMARY OF THE INVENTION

The invention thus provides an optimized inductive sensor of the type comprising a primary winding fed with an alternating current supplied by an excitation device and multiple secondary windings subject co the magnetic field created by the primary winding and providing electric signals at the output terminals representative of the variations in the magnetic field due to the presence of a metallic target with discontinuities, the said electric signals being applied to an amplification-demodulation circuit followed by a processing circuit for the demodulated signals, characterized in that:

the secondary windings have minimum dimensions compatible with detection of the signals induced by the variations in the magnetic field, in such a manner as to be able to associate a maximum number of secondary winding with a primary winding between two discontinuities of the target, and the output terminals of the secondary windings are connected to interconnection means which effect adaptive connection of the said output terminals in such a manner as to connect the secondary windings as a function of the discontinuities of the target, in a stored form or as a desired transfer function.

The optimized sensor of the invention can advantageously be associated with an electronic interface circuit through which one or more of the following functions can be executed:

local or global analysis or analysis according to given groupings of the signals provided by the secondary windings;

grouping of the signals provided by the secondary windings according to a defined representation;

grouping of the signals provided by the secondary windings according to a configuration determined by the interface circuit itself to apply a specified transfer function.

In the case of adaptation to the marks of the target, couples of secondary windings are grouped by the said interconnection means to obtain signals whose signal-to-noise ratio is as good as possible.

The interconnection means can be realized by metallic conductor elements, by electronic switches whose opening and closing are effected through electric signals provided by an adaptive circuit. The interconnections can also be determined by an auto-calibration procedure. They can for example be realized by means of predefined metal connections or miniature electronic switches, whose closing depends on the desired regrouping, or on the local or global transfer function which it is desired to implement. Moreover, it is possible to add a calculation and/or weighting function to all or a part of the secondary windings.

BRIEF DESCRIPTION OF THE DRAWINGS

Other features and advantages of the present invention will appear from a reading of the following description of one particular embodiment, the said description being given with reference to the accompanying drawings, in which.

BRIEF DESCRIPTION OF THE PREFERRED EMBODIMENTS

Figure 1:
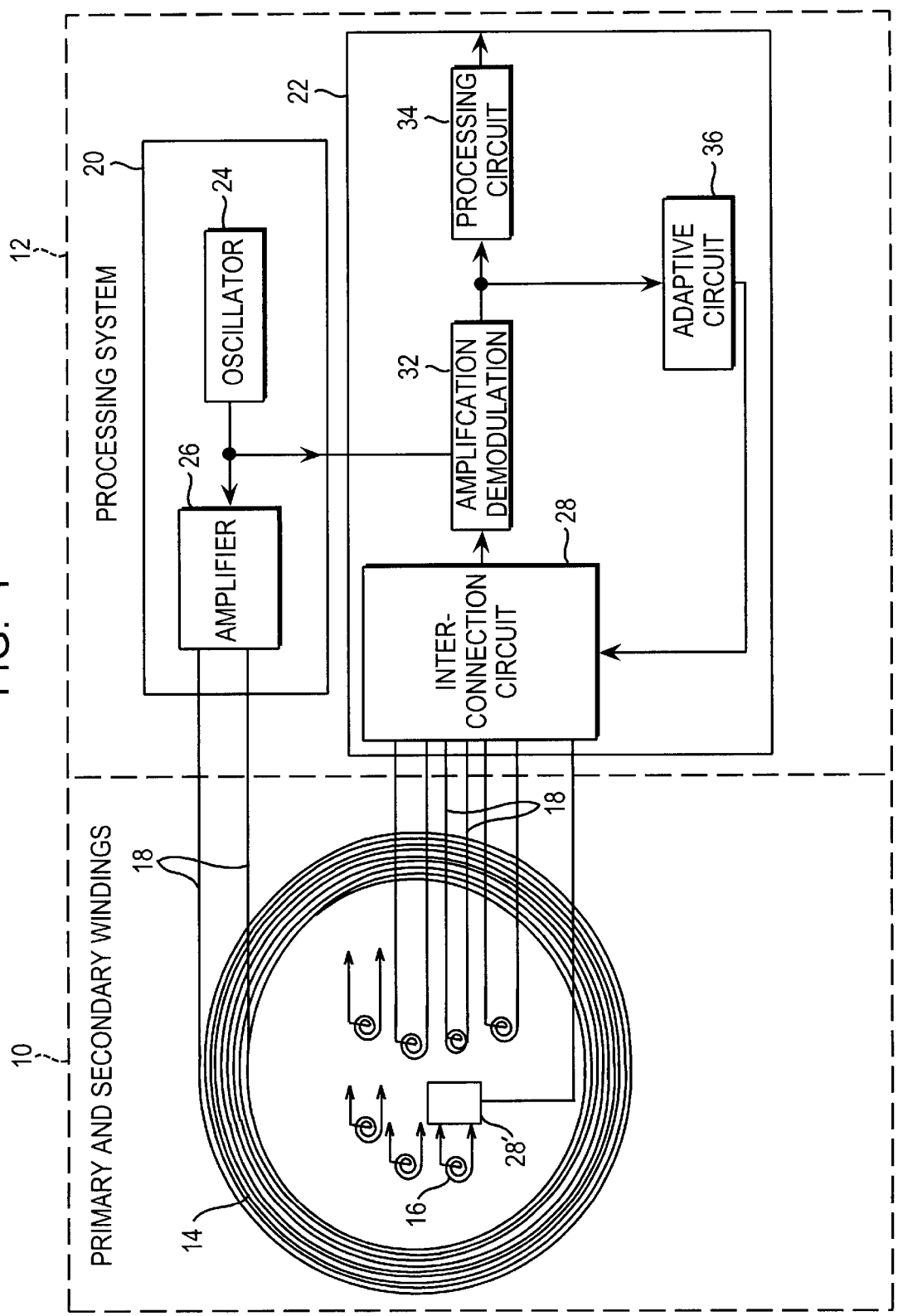
FIG. 1 is a functional diagram of an inductive sensor with the features of the present invention.

An inductive sensor according to the invention is shown in FIG. 1. It comprises two parts; the one, referenced 10, comprises the primary and secondary windings 14 and 16 respectively and the other, referenced 12, is formed by a processing system for the electric signals applied to the primary winding 14 and those provided by the secondary windings 16.

According to the invention, a plurality of receiving secondary windings 16 are associated with respective exciting primary windings 14. The input terminals of the primary winding 14 and the output terminals of the secondary windings 16 are connected to the processing system 12 by conductors 18. The processing system 12 comprises an electronic excitation device 20 which provides the electric excitation signal for the primary winding or exciting coil 14 and an electronic device 22 for processing the electric signals appearing at the output terminals of the secondary windings 16.

The electronic excitation device 20 essentially comprises an oscillator 24, whose alternating signal is amplified in an amplifier 26 before being applied to the input terminals of the primary winding 14.

The electronic processing arrangement 22 comprises, according to the invention:

an interconnection circuit 28 for the output terminals of the secondary windings 16 such as to group the receiving coils according to a predefined representation, a desired transfer function or in such a manner as to ensure the best possible optimum grouping, where the latter can be determined by auto-calibration means.

a local processing circuit 28 for the signals provided by the receiving coils, for effecting a calculation or a given transfer function, an amplification-demodulation circuit 32 comprising one amplifier-demodulator per grouping of secondary windings for example, an adaptive circuit 36 for adapting the interconnection 28 as a function of the results of the processing effected, and a processing circuit 34 for the demodulated signals.

The interconnection circuit 28 which effects the optimum grouping of the secondary winding to obtain a selected representation can be realized directly on the substrate which supports the secondary windings, as has been described in the patent applications referenced above. In the general case, such as is shown in FIG. 1, the interconnection circuit 28 allows connection in series of any grouping of receiving windings in such a manner that this grouping corresponds to the desired configuration. This configuration can be fixed and the interconnection circuit 28 is then formed by simple connections, resulting in the series connection of the receiving coils pertaining to the said grouping. It can equally be capable of modification and, in this case, the interconnection circuit advantageously has the form of a matrix of rows and columns with interconnection means between each row and each column. Each row is moreover connected to first terminal of a receiving winding and each column is connected to a second terminal of a receiving winding. The interconnection means can be of any known type, such as electronic mini-switches, fusible links, etc. They should however enable realization of any form of grouping of the receiving coils to obtain the desired function. The establishment of a connection between a row and a column of the matrix is controlled by the adaptive circuit 36, whose purpose and function will be explained in the course of the description.

The interconnection circuit 28 has been located ahead of the amplification-demodulation circuit 32 but it can equally be located after the amplification-demodulation circuit 32.

The processing circuit 34 can be of any known type, for example the type used to process optical images, often called an "artificial retina", for detecting the contour, the position, the movement, the orientation and the speed of objects. The circuit 34 can for example extract the contour of a mark (or tooth) of the target and adapt the configuration, through the circuit 28, of the receiving coils, in such a manner that it corresponds to this contour. Reference may be made in particular to the article by P. Vernier et al with the title "An integrated cortical layer for orientation enhancement" appearing in IEEE Journal of Solid-State Circuits, Vol. 32, No. 2, Feb. 1997.

In order to effect the operation of demodulation in the amplification-demodulation circuit 32, this receives the electric signal from the oscillator 24 of the excitation device 20, which serves as the reference signal for the demodulators.

Figure 2:
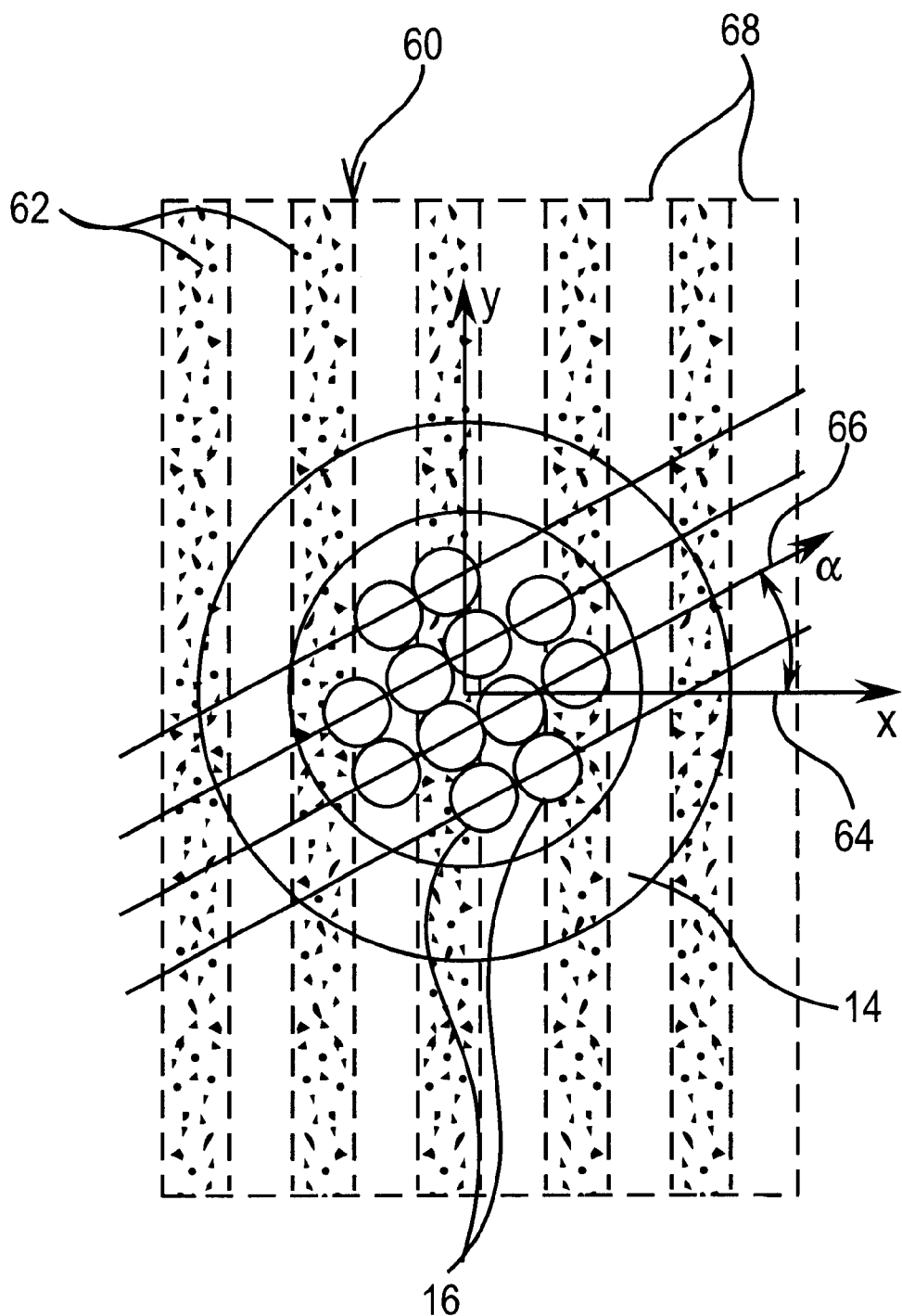
FIG. 2 is a diagram showing one particular arrangement of a plurality of secondary windings relative to the teeth of a wheel.
Figure 3:
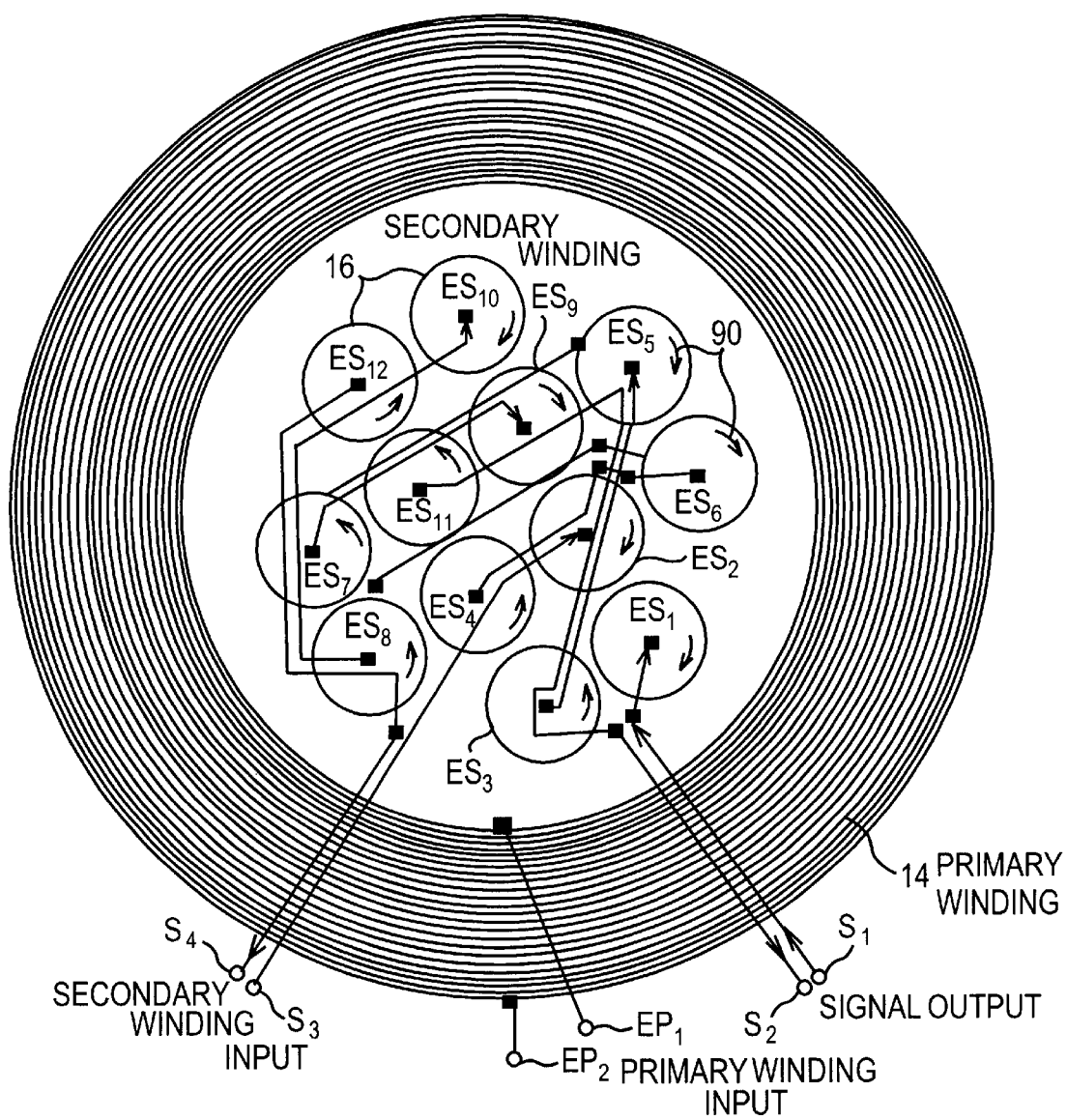
FIG. 3 is a diagram showing a wiring of the various secondary windings of the sensor of FIG. 2 in the case of adapting to a target of known pitch.

FIG. 2 is a diagram which shows the positions of the secondary winding of an inductive sensor relative to the vertical teeth of a target, while FIG. 3 is a diagram which shows an embodiment of a wiring circuit between the couples of secondary windings such as is defined by the diagram of FIG. 2.

FIGS. 2 and 3 show an example of the interconnection of the receiving coils meeting a predetermined configuration. The exciting primary winding 14 is associated with twelve receiving secondary windings 16, referenced ES1 to ES12 in FIG. 3 and the whole unit is placed near to a toothed wheel 60 having teeth 62 with a pitch equal to T. The secondary windings have an external diameter L which is greater than T/2, the result of which is that the secondary windings cannot be aligned along the direction of displacement 64 of the teeth and for a maximum differential signal, but are aligned along a direction 66 making an angle $\alpha$ with the direction 64, such that tan a $\alpha=\frac{1}{2}$.

The twelve secondary windings should be grouped two by two, i.e. in couples, in such a manner that the flanks that they detect will be of opposite senses, i.e. one winding should be in correspondence with a transition in the sense of tooth-to-gap while the other is in correspondence with a transition in the sense of gap-to-tooth.

Furthermore, the differential signals provided by the couples of secondary windings which correspond to the same type of transition are added to augment the signal. Thus the signals of the couples $(ES_1, ES_3)$, $(ES_5, ES_7)$ and $(ES_9, ES_{11})$ are added by suitable wiring to obtain a sum signal between the output terminals $S_2$ and $S_1$, while the signals of the couples $(ES_2, ES_4)$, $(ES_6, ES_8)$ and $(ES_{10}, ES_{12})$ are added by appropriate wiring to obtain a sum signal between the output terminals $S_4$ and $S_3$.

In FIG. 3 the terminals $EP_1$, and $EP_2$ are the input terminals of the primary winding 14 and the arrows 90 indicate the sense of each secondary winding. In the device which is described with reference to FIGS. 2 and 3, the interconnection circuit 28 has been implemented directly on the substrate in the immediate vicinity of the secondary windings $ES_1$ to $ES_{12}$ as a function of the pitch T of the teeth of the wheel 60, the diameter L of the secondary windings and the number of secondary windings. This corresponds to adaptation "by hand" in accordance with the problem to be resolved.

Figure 4:
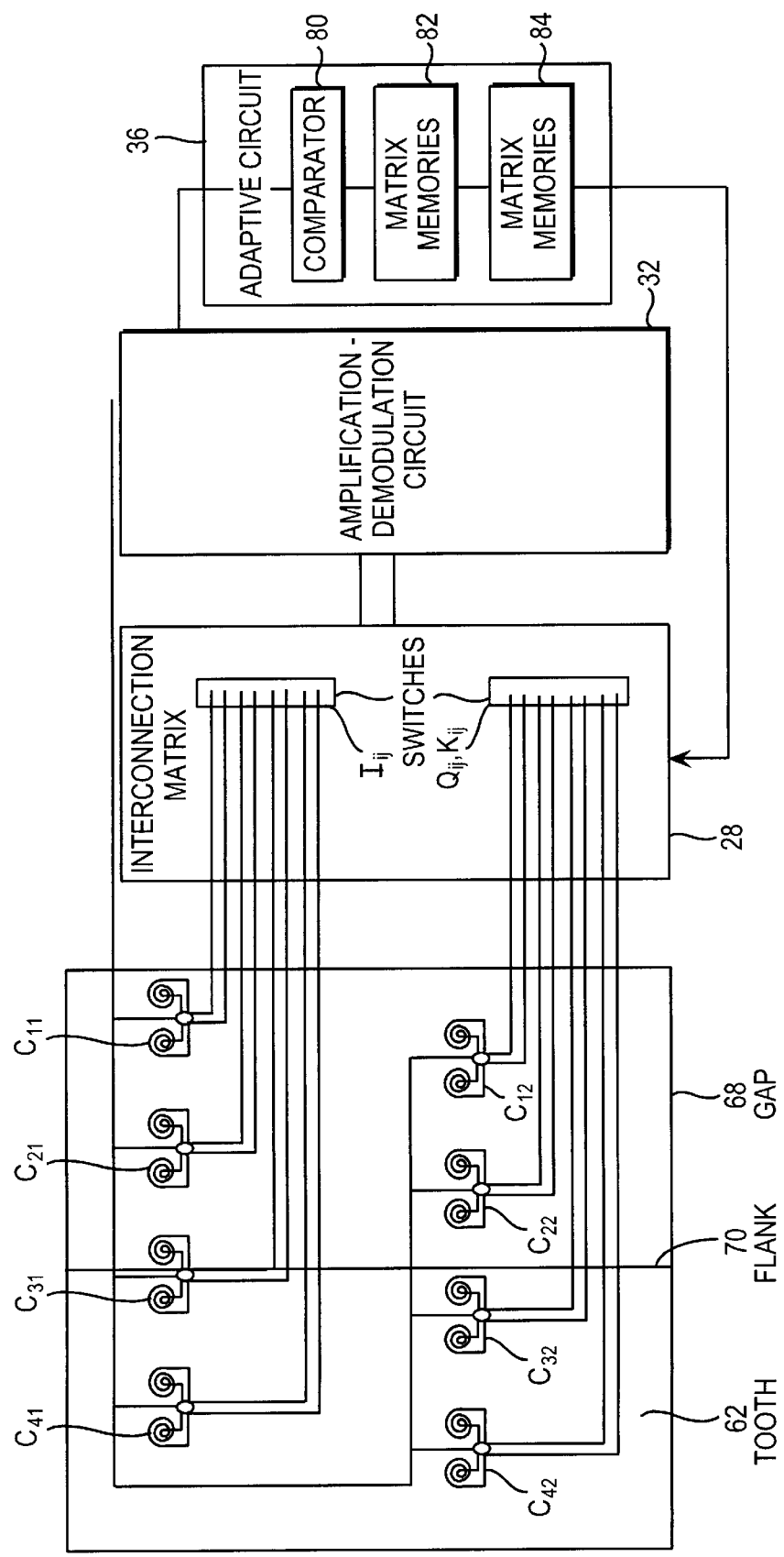
FIG. 4 is a diagram showing an embodiment of auto-calibration of an inductive sensor to the pitch of a target.

The device which is described with reference to FIG. 4 corresponds to an "automatic" adaptation of the sensor to a differential configuration and to the pitch of the target. In this FIG. 4 there is represented schematically only the receiving part disposed in front of a single tooth 62 followed by a gap 68, the tooth and the gap being separated by a flank 70 which forms a line of magnetic discontinuity.

The secondary windings of a differential couple are located side by side and the couples are denominated in the form of a matrix, each couple thus being referenced $C_{ij}$. The 4 couples of the second row with j=2 are staggered with reference to those of the first row with j=1. The output terminals of the couples $C_{ij}$ are connected to the interconnection matrix 28, whose output terminals are connected to the amplification-demodulation circuit 32.

The adaptive circuit 36 comprises a comparator 80 and two matrix memories 82 and 84.

The interconnection matrix 28 comprises a series of pairs of switches $I_{ij}$, one pair per couple $C_{ij}$ in such a manner as to connect a couple selectively to the corresponding amplifier-demodulator circuit. It also comprises other switches, referenced $Q_{ij}$ and $K_{ij}$, which are provided to effect the interconnection between the different couples in such a manner as to group them according to the results of the auto-calibration.

The auto-calibration is effected by controlling the switches $I_{ij}$ when the target is stationary, so as to measure the output signal of each couple $C_{ij}$. When the amplitude of the signal is greater than a certain threshold, this signifies that the couple is in correspondence with a flank 70 (couple $C_{31}$) and this is stored in the memory 82 as the binary signal 1. All the other couples are outside a flank and the detected signals are less than the threshold; they are stored as a binary 0 digit. A matrix of 1's and 0's is thus obtained which, for the case of FIG. 4 is:

0100
0000

Such a matrix signifies that the couple $C_{31}$ is in correspondence with the flank 70, the couples $C_{41}$, $C_{23}$ and $C_{42}$ are facing a tooth while the couples $C_{11}$, $C_{21}$, $C_{12}$ and $C_{22}$ are facing a gap. It is thus deduced that it is necessary to add the signals of the couples in front of a tooth and to subtract the signals of the couples in front of a gap and this is realized by the switches $Q_{ij}$ and $K_{ij}$, whose opening or closing is controlled by the binary values of a matrix derived from the preceding, namely:

1100
1100 where p=1 means addition of the signals and p=0 means subtraction of the signals.

The foregoing description shows that the steps of an auto-calibration procedure of an inductive sensor consist of:
 (1) measuring the output signal of each couple of secondary windings $C_{ij}$.
 (2) comparing the measured signal with a threshold and assigning it the binary value 1 or 0, according to whether it is above or below the said threshold,
 (3) assigning the binary value 1 or 0 to the elements of a first matrix representing the layout of the couples of secondary windings $C_{ij}$,
 (4) transforming this first matrix into a second matrix representing groupings of couples of secondary windings to be effected according to the discontinuity to be detected, and
 (5) deriving control signals for the switches of the interconnection means on the basis of this second matrix.

What is claimed is:

1. An inductive sensor for detecting movements and magnetic images of at least one target, comprising a primary winding (14) fed with an alternating current supplied by an excitation device (20) and a large number of secondary windings (16) subject to the magnetic field created by the primary winding (14) and providing electric signals at their output terminals representative of variations in the magnetic field due to the presence of a metallic target with discontinuities, said electric signals being applied to an amplification-demodulation circuit (30) followed by a processing circuit (34) for the demodulated signals, wherein
 the secondary windings (16) are of minimum dimensions compatible with detection of the signals induced by the variations in the magnetic field, in such a manner as to be able to associate a maximum number of secondary windings with a primary winding between two discontinuities of the target, and
 the output terminals of the secondary windings are connected to interconnection means (28) and to the amplification-demodulation circuit which effect adaptive wiring of said output terminals in such a manner as to connect the windings among themselves for at least one of: (1) obtaining an electric signal from at least one of all of the secondary windings, a partial grouping and a grouping which is variable with time, said groupings being effected by means of said interconnection means, (2) grouping the receiving windings among themselves in accordance with a predetermined representation, said representation being related to at least one of the shape, the structure and the number of said at least one target, and (3) grouping the receiving coils among themselves in accordance with an auto-reconfiguration procedure effected in accordance with detection of at least one of movement and magnetic imaging of at least one target.

2. The inductive sensor according to claim 1, wherein said interconnection means (28) comprises interconnection means for grouping the secondary windings among themselves in such a manner as to allow detection of discontinuities of the target to maximize one of a target signal value and a mounting error correction value.

3. The inductive sensor according to claim 1, wherein the interconnection means (28) are metallic conductor elements.

4. The inductive sensor according to claim 1, wherein the interconnection means (20) comprise switches controlled by electric signals ($M_{ij}$, $I_{ij}$, $Q_{ij}$ and $K_{ij}$).

5. The inductive sensor according to claim 4, further comprising an adaptive circuit (36) which provides the control signals for the switches (Mij, Iij, Qij and Kij) of the interconnection means (28), said control signals (p) being determined by a calibration procedure 38.

6. An auto-calibration procedure for an inductive sensor according to claim 5, wherein said secondary windings are couples of secondary windings ($C_{ij}$), the procedure comprising the steps of:
 measuring output signals of each couple of said secondary windings ($C_{ij}$),
 comparing the measured signal with a threshold and assigning the measured signal the binary value 1 or 0 according to whether it is above or below said threshold,
 applying the binary value 1 or 0 to the elements of a first matrix representing the layout of the couples of secondary windings ($C_{ij}$),
 transforming said first matrix into a second matrix representing groupings of couples of secondary windings to be effected in accordance with the discontinuity to be detected, and
 deriving control signals for the switches of the interconnection means on the basis of said second matrix.

7. An inductive sensor according to claim 1, wherein said interconnection means is one of an active interconnection means and a passive interconnection means.

8. An inductive sensor according to claim 1, wherein said groupings are effected by means of said interconnection means depending on at least one of results of calculation, effecting a desired transfer function and results of a desired averaging function.

* * * * *